United States Patent
Schulman et al.

(10) Patent No.: US 7,286,883 B2
(45) Date of Patent: Oct. 23, 2007

(54) MINIATURE IMPLANTABLE CONNECTION METHOD

(75) Inventors: Joseph H. Schulman, Santa Clarita, CA (US); Janusz Kuzma, Parker, CO (US)

(73) Assignee: Alfred E. Mann Foundation For Scientific Research, Santa Clarita, CA (US)

( * ) Notice: Subject to any disclaimer, the term of this patent is extended or adjusted under 35 U.S.C. 154(b) by 379 days.

(21) Appl. No.: 11/152,444

(22) Filed: Jun. 13, 2005

(65) Prior Publication Data
US 2005/0234318 A1   Oct. 20, 2005

Related U.S. Application Data

(62) Division of application No. 09/971,849, filed on Oct. 4, 2001, now Pat. No. 6,947,782.

(60) Provisional application No. 60/299,106, filed on Jun. 18, 2001.

(51) Int. Cl.
*A61N 1/05*   (2006.01)

(52) U.S. Cl. ...................... 607/116; 600/373

(58) Field of Classification Search ..................... None
See application file for complete search history.

(56) References Cited

U.S. PATENT DOCUMENTS

| | | | |
|---|---|---|---|
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,551,345 B2 * | 4/2003 | Vogel et al. ................... 607/1 |

* cited by examiner

*Primary Examiner*—Kristen D. Mullen
(74) *Attorney, Agent, or Firm*—Gary D. Schnittgrund

(57) ABSTRACT

Methods are utilized for connecting electrically conductive wire to a miniature, implantable sensor or stimulator device for detecting electrical signals or stimulating living tissue. The implantable device has an electrically conductive end on its case which is intimately connected to a doorknob electrode for communicating electrical signals between the living tissue and the device by a biocompatible wire. A spring clip removably attaches to the doorknob electrode so that the wire may be easily attached to the doorknob electrode during surgery. An insulating rubber boot, which may be silicone, surrounds the case end, doorknob electrode, and spring clip to isolate the living tissue from the conductive components. The components are all biocompatible materials.

15 Claims, 12 Drawing Sheets

MINIATURE IMPLANTABLE CONNECTION METHOD

CROSS REFERENCE TO RELATED APPLICATION

This application is a divisional of U.S. patent application Ser. No. 09/971,849, filed Oct. 4, 2001; now U.S. Pat. No. 6,947,782 which claims the benefit of U.S. Provisional Application No. 60/299,106, filed on Jun. 18, 2001.

BACKGROUND OF THE INVENTION

1. Field of the Invention

This invention relates to methods of connecting electrical conducting wires to a miniature implantable device to minimize risk to the living tissue during and after surgery.

2. Description of Related Art including Information Disclosed under 37 CFR 1.97 and 1.98

Neurological disorders are often caused by neural impulses failing to reach their natural destination in otherwise functional body systems. Local nerves and muscles may function, but, for various reasons, such as injury, stroke, or other cause, the stimulating nerve signals do not reach their natural destination. For example, paraplegic and quadriplegic animals have intact nerves connected to functioning muscles and only lack the brain-to-nerve link. Electrically stimulating the nerve or muscle can provide a useful muscle contraction.

Further, implanted devices may be sensors as well as stimulators. In either case, difficulties arise both in providing suitable, operable stimulators or sensors which are small in size and in passing sufficient energy and control information to or from the device, with or without direct connection, to satisfactorily operate them. Miniature monitoring and/or stimulating devices for implantation in a living body are disclosed by Schulman, et al. (U.S. Pat. No. 6,164,284), Schulman, et al. (U.S. Pat. No. 6,185,452), and Schulman, et al. (U.S. Pat. No. 6,208,894) all incorporated in their entirety herein by reference.

It must be assured that the electrical current flow does not damage the intermediate body cells or cause undesired stimulation. Anodic or cathodic deterioration of the stimulating electrodes must not occur.

In addition, at least one small stimulator or sensor disposed at various locations within the body may send or receive signals via electrical wires. The implanted unit must be sealed to protect the internal components from the body's aggressive environment. If wires are attached to the stimulator, then these wires and the area of attachment must be electrically insulated to prevent undesired electric signals from passing to surrounding tissue.

Miniature stimulators offer the benefit of being locatable at a site within the body where a larger stimulator cannot be placed because of its size. The miniature stimulator may be placed into the body by injection. The miniature stimulator offers other improvements over larger stimulators in that they may be placed in the body with little or no negative cosmetic effect. There may be locations where these miniature devices do not fit for which it is desired to send or receive signals. Such locations include, but are not limited to, the tip of a finger for detection of a stimulating signal or near an eyelid for stimulating blinking. In such locations, the stimulator and its associated electronics are preferably located at a distance removed from the sensing or stimulating site within the body; thus creating the need to carry electrical signals from the detection or stimulation site to the remote miniature stimulator, where the signal wire must be securely fastened to the stimulator.

Further, the miniature stimulator may contain a power supply that requires periodic charging or require replacement, such as a battery. When this is the case, the actual stimulation or detection site may be located remotely from the stimulator and may be located within the body, but removed a significant distance from the skin surface. By having the ability to locate the miniature stimulator near the skin while the stimulation site is at some distance removed from the skin, the miniature stimulator and its associated electronics can be more effectively replaced by a surgical technique or more efficiently recharged through the skin by any of several known techniques, including the use of alternating magnetic fields. If the electronics package is replaced surgically, then it is highly desirable to have the capability to reconnect the lead wires to the miniature stimulator via an easy, rapid and reliable method, as disclosed herein.

BRIEF SUMMARY OF THE INVENTION

The instant invention relates to a method for connecting an electrically conductive wire to a miniature, implantable sensor or stimulator. A method of communicating electrical signals between living tissue and an implantable miniature device configured for monitoring and/or affecting body parameters includes snapping a spring clip connector over a doorknob electrode and attaching a conductive wire having a first end for electrical coupling to a selected portion of living tissue and a second end for coupling to the spring clip connector.

The first end of the conductive wire is in contact with living tissue and the miniature implantable device is remote from the first end of the conductive wire. An insulating rubber boot may be placed over the spring clip connector, conductive wire second end, and doorknob electrode. The rubber boot may be silicone.

The spring clip connector may be selected from the group consisting of titanium, titanium alloy, platinum, iridium, platinum-iridium, stainless steel, tantalum and niobium. The doorknob electrode may be a selected from the group consisting of titanium, titanium alloy, platinum, iridium, platinum-iridium, stainless steel, tantalum, and niobium.

The spring clip connector may have at least one prong for grasping said doorknob electrode.

OBJECTS OF THE INVENTION

It is an object of the invention to provide a method of connecting at least one wire to a miniature stimulator in a body.

Other objects, advantages and novel features of the present invention will become apparent from the following detailed description of the invention when considered in conjunction with the accompanying drawings.

DETAILED DESCRIPTION OF THE INVENTION

Figure 1:
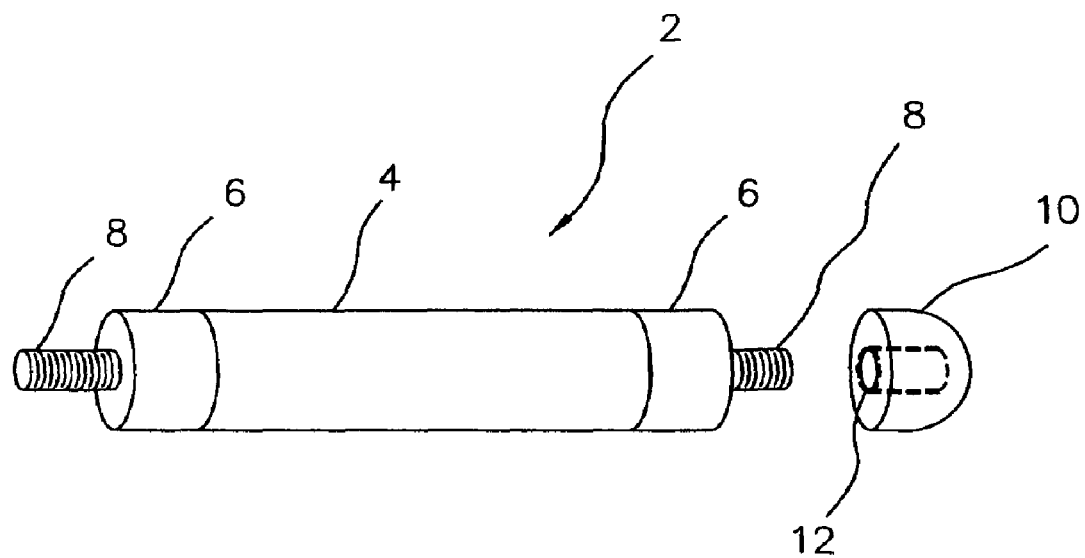
FIG. 1 illustrates a perspective view of the miniature stimulator with a threaded connector and nut.
Figure 43:
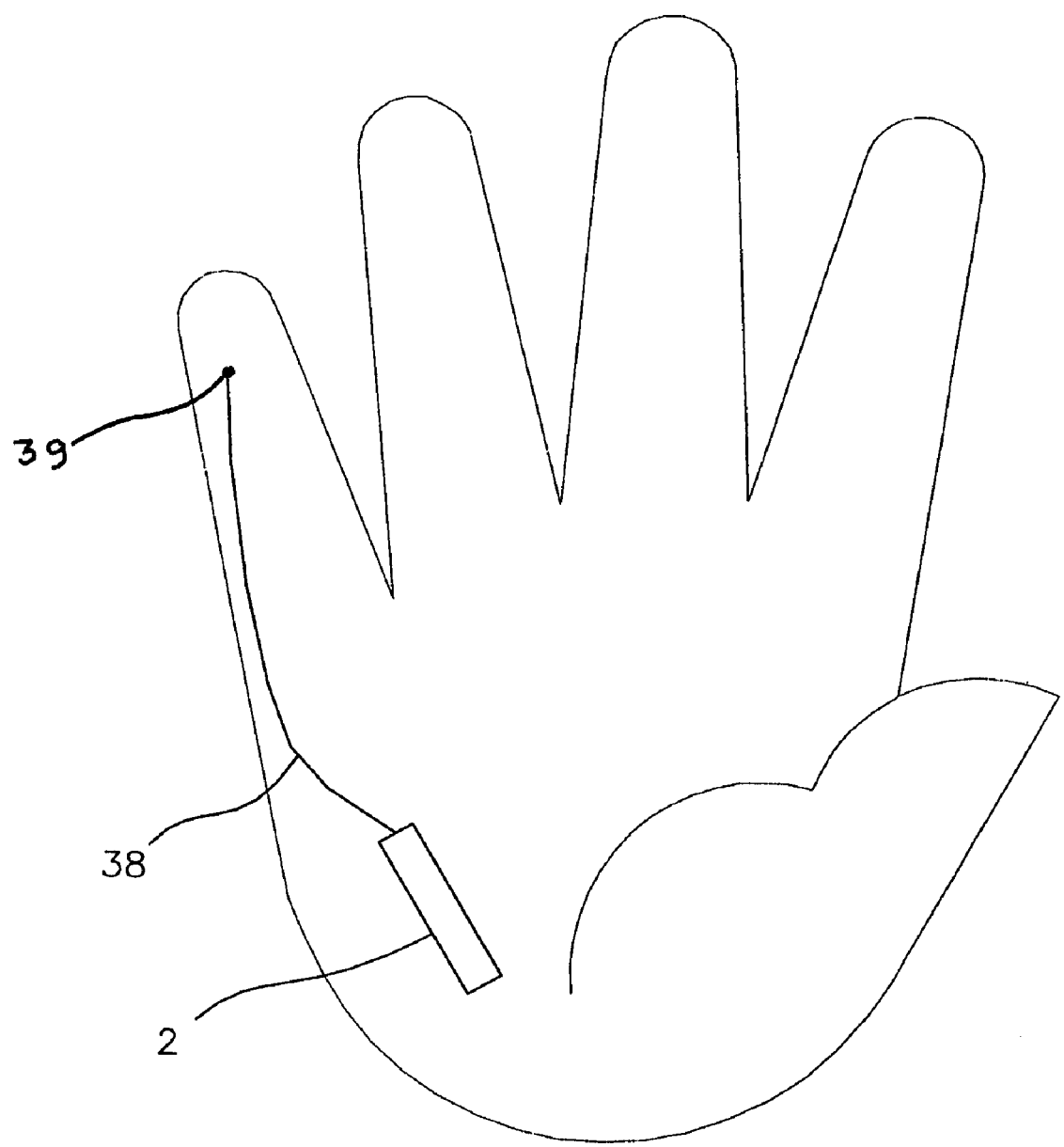
FIG. 43 is a hand showing placement of an implantable miniature device with a wire lead that carries electrical signals to a fingertip.

An implantable miniature stimulator 2 is illustrated in FIG. 1. FIG. 43 represents a typical placement of the implantable miniature stimulator 2 at a location that is remote from the site that is to be stimulated, in this case a fingertip, where an electrically conductive wire 38 carries the electrical signal to an electrode 39 at the stimulation site. Typical dimensions for this device are about 5 to 60 mm in length and about 1 to 6 mm in diameter. (See, for example, U.S. Pat. Nos. 6,164,284, 6,185,452, and 6,208,894 which are incorporated herein by reference in their entirety.) While element 2 is generally described as a stimulator, it is recognized that the present invention is equally applicable when element 2 is operable as a sensor or as a stimulator and a sensor. Stimulator 2 includes insulating case 4, which typically is hollow and contains an electronics package and a power source, such as a battery, capacitor, magnetic field to electricity converter, and electrically conductive case ends 6, each of which has an electrically conductive electrode 8 which conducts electrical signals from a stimulator and/or to a sensor, depending upon the design and function of that particular miniature stimulator 2. Stimulator 2 may have at least one electrode, e.g., 2-8 or more, depending upon its particular design and function, although, for illustrative purposes, only two electrodes are shown in FIG. 1. Electrically conductive electrodes 8 are shown threaded in FIG. 1, although alternate embodiments are shown in other figures and are discussed herein.

Insulating case 4 contains the electronics, which may include a battery or other energy storage device and signal generating or receiving circuitry and is made of an electrically insulating material that is capable of being hermetically sealed and that is also biocompatible, such as plastic or ceramic. The plastic may be epoxy, polycarbonate, or plexiglass. The ceramic may be alumina, glass, titania, zirconia, stabilized-zirconia, partially-stabilized zirconia, tetragonal zirconia, magnesia-stabilized zirconia, ceria-stabilized zirconia, yttria-stabilized zirconia, or calcia-stabilized zirconia, and in a preferred embodiment, insulating case 4 is yttria-stabilized zirconia, although other insulating materials may also be used. The insulating case 4 must be a material that is biocompatible as well as capable of being hermetically sealed, to prevent permeation of bodily fluids into the case.

The electrically conductive case end 6 is preferably a biocompatible, non-corrosive material, such as titanium or a titanium alloy, although other metals such as platinum, iridium, platinum-iridium, stainless steel, tantalum, niobium, or zirconium may be used. The preferred material is Ti-6 Al-4V. An alternate preferred material is platinum-iridium.

If any electrically conductive electrode is not being used while the stimulator is in the body, then the electrode may be insulated to prevent stimulation of nearby tissue. Protective nut 10 is either an insulator or an electrically conductive conductor. If it is an electrical conductor, then it is an extension electrode of electrically conductive case 6. It is placed over the unused electrically conductive electrode 8 such that protective nut threaded hole 12 is tightly screwed onto threaded electrically conductive electrode 8. In a preferred embodiment, the threads on threaded electrically conductive electrode 8 are 0 80 threads. In order to avoid growth of tissue into joints, such as the joint formed between protective nut 10 and electrically conductive case end 6, it is preferable that any gap be less than 7 microns.

Figure 2:
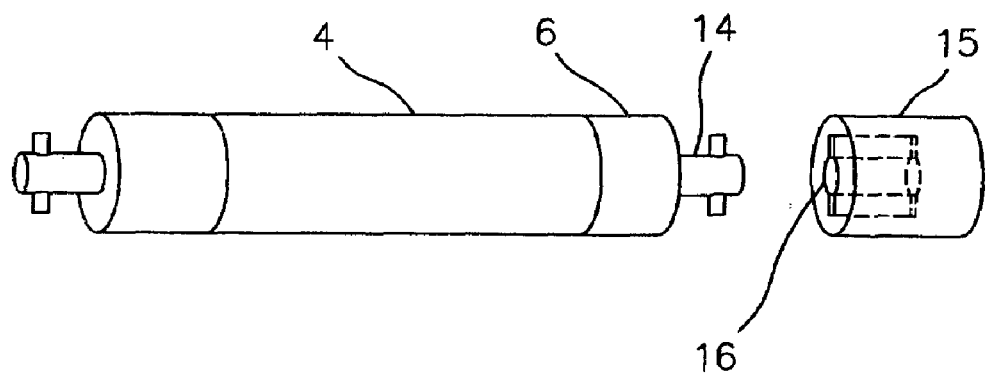
FIG. 2 illustrates a perspective view of the miniature stimulator with a bayonet connector and nut.
Figure 3:
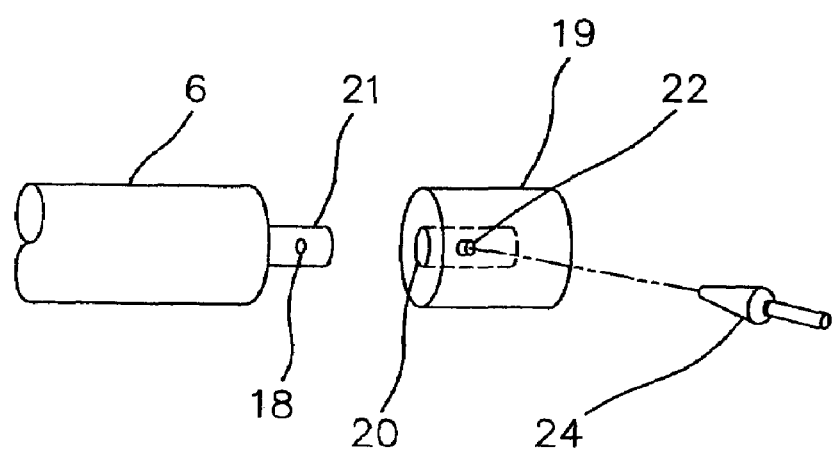
FIG. 3 illustrates a perspective view of the miniature stimulator with a pin connector and nut.

An alterative embodiment is illustrated in FIG. 2 where bayonet electrode 14 is covered by protective nut 15 that contains bayonet mount 16. Yet another embodiment of miniature stimulator 2 is illustrated in FIG. 3, where electrically conductive electrode 8 is now stud electrode 21, a smooth stud, which has electrode through-hole 18 passing radially through and intersecting with the longitudinal axis of stud electrode 21. Stud protective nut 19 is placed onto stud electrode 21 such that protective nut mounting hole 20 fits over stud electrode 21 while protective nut through-hole 22 is aligned with electrode through-hole 18. Protective nut through-hole 22 is positioned such that it passes radially through and intersects with the longitudinal axis of protective nut 19 and such that nut 19 fits very snugly against electrically conductive case end 6. Breakaway pin 24 is placed into protective nut through-hole 22 and into electrode through-hole 18. After alignment of protective nut 19 onto electrode 21 is complete, the protruding portion of breakaway pin 24 is broken off and discarded.

Figures 4, 5:
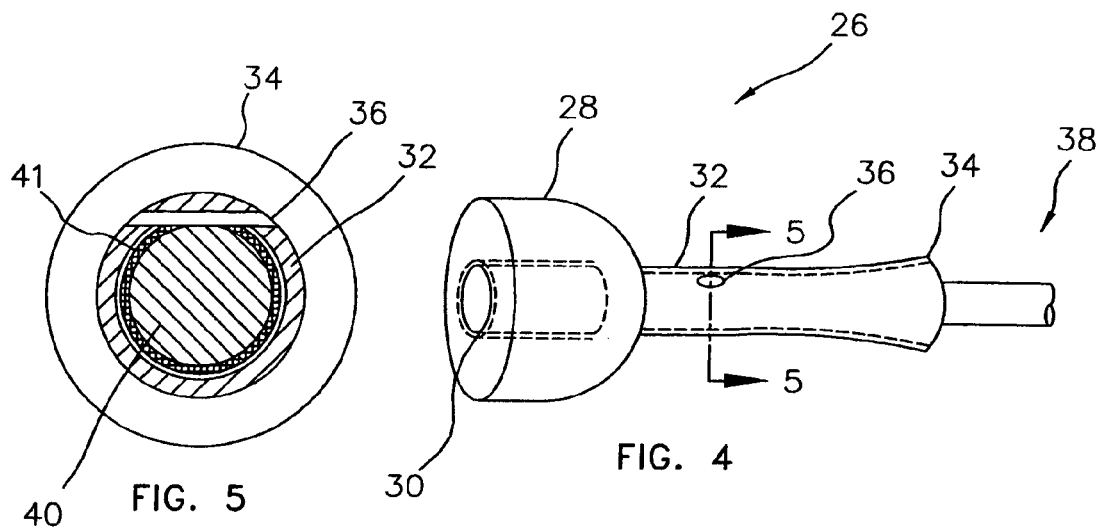
FIG. 4 illustrates a perspective view of the smooth nut with a flare nut cap.
FIG. 5 is a cross-section through the flare nut wire insertion.
Figure 6:
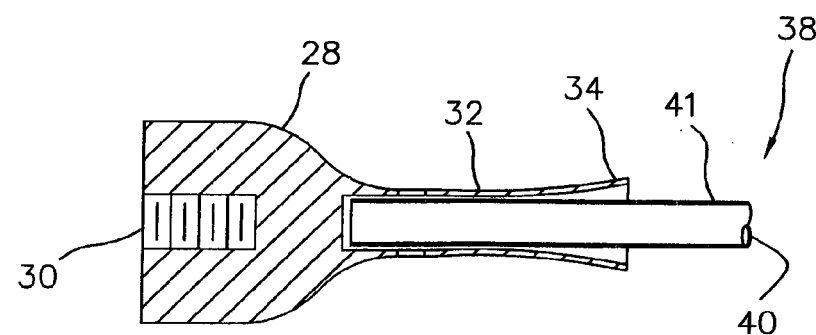
FIG. 6 is a cross-sectional view of the smooth cap with flare insertion.

A preferred method of attaching an electrically conductive wire 38 to a miniature stimulator 2 (see FIG. 1) is illustrated in FIGS. 4, 5, and 6 wherein flare nut 26 is comprised of protective nut 28, which contains flare nut mounting hole 30. Threaded flare nut mounting hole 30 is positioned over electrode 8 (see FIG. 1) and tightened by screwing onto the threads. Flare nut 26 also contains flare nut wire receptor 32 which has flare 34 on its extension pointed away from protective nut 28. Because of the small diameter of wire used in this application, flare 34 is provided for ease of placement of electrically conductive wire 38 into flare 34. Offset through-hole 36 passes through flare nut wire receptor 32 in a plane that is perpendicular to the longitudinal axis of flare nut 26. Offset through-hole 36 preferably does not intersect with the longitudinal axis of nut 26, but is intentionally offset to penetrate wire insulator 41 (see FIG. 6) and to intersect with the outer diameter of wire conductor 40. Thus when a pin, not illustrated, is placed in offset through-hole 36, wire conductor 40 is contacted, creating an electrically conductive path between wire conductor 40 and protective nut 28.

The cross-sectional view of FIG. 5 illustrates the offset alignment of offset through-hole 36 with respect to the longitudinal axis of flare nut wire receptor 32. Wire conductor 40 is intersected by offset through-hole 36 such that wire insulator 41 will be penetrated and wire conductor 40 will be contacted by a pin inserted in offset through-hole 36. Electrically conductive wire 38, shown in FIG. 6 is comprised of wire conductor 40 within wire insulator 41. Alternately, wire insulator 41 may be stripped from an end portion of wire conductor 40, to help insure good electrical contact between conductor 40 and flare nut wire receptor 32.

In a preferred embodiment, wire conductor 40 is a highly conductive metal that is also benign in the body, such as MP35, although stainless steel or an alloy of platinum-iridium may also be used. Preferably, the wire has a diameter of approximately 0.003 inches. It is contained in wire insulator 41 to electrically isolate it from the body tissue and fluids and, in a preferred embodiment, wire insulator 41 is Teflon-coated silicone.

Figures 7, 8:
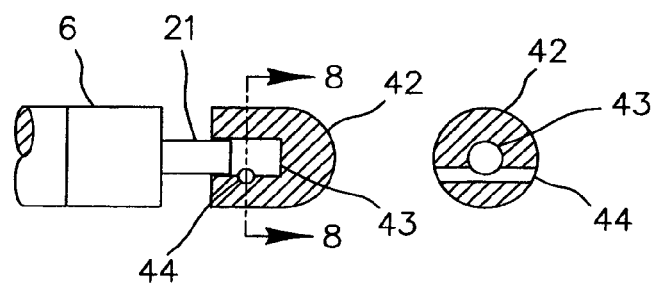
FIG. 7 is a longitudinal section through the protective nut showing an offset mounting hole.
FIG. 8 is a cross-section through the protective nut showing the offset mounting hole.

An alternate method of attaching an electrically conductive wire (not shown) to electrically conductive case end 6 is shown in FIG. 7, where an electrically conductive wire is attached to smooth stud electrode 21 by placing smooth protective nut 42 over stud electrode 21 by aligning protective nut mounting hole 43 with stud electrode 21 and engaging them. Offset through-hole 44 is of a diameter that allows an insulated wire to pass therethrough and it is aligned such that when smooth protective nut 42 is pushed onto stud 21, the electrically conductive wire is contacted and crushed, thereby making electrical contact between the electrically conductive wire and stud electrode 21. A cross-sectional view through protective nut 42, illustrated in FIG. 8, shows the alignment of offset through-hole 44 with respect to protective nut mounting hole 43. Smooth protective nut 42 is retained on stud 21 by virtue of the frictional force generated by a crushed wire present in offset through-hole 44 as protective nut 42 is placed on stud electrode 21.

Figure 9:
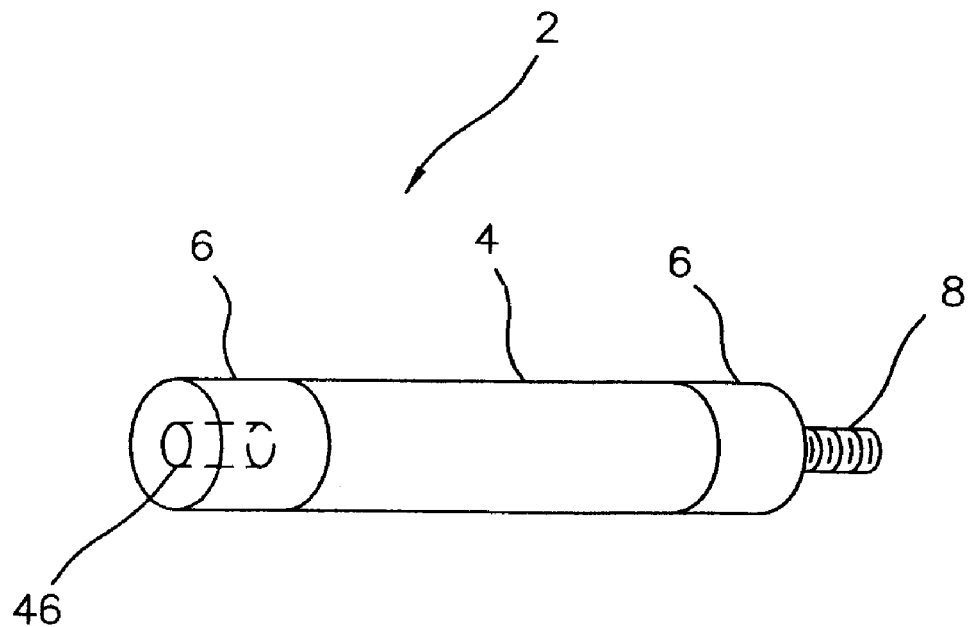
FIG. 9 illustrates a stimulator with a hole and pin electrode.
Figure 10:
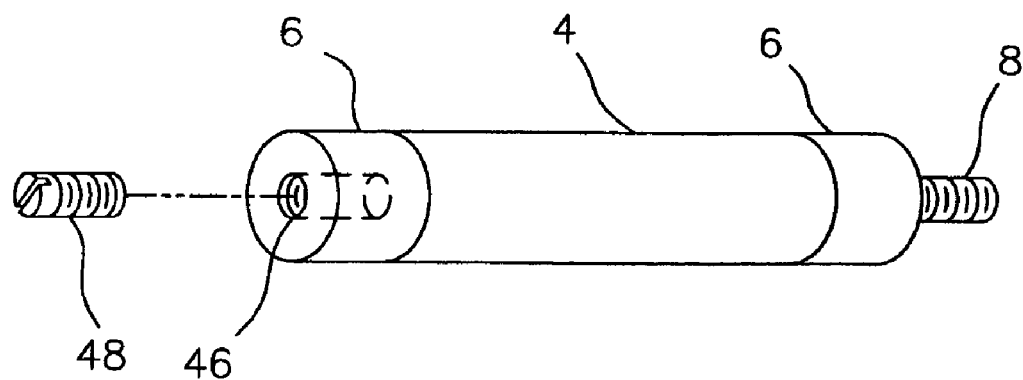
FIG. 10 illustrates a stimulator with a hole and pin electrode and an electrode plug.

In an alternate embodiment, shown in FIG. 9, miniature stimulator 2 has at one end threaded electrically conductive electrode 8 and at the other end threaded electrode hole 46. Alternate embodiments contain various combinations of electrically conductive electrodes 8 and electrode holes 46. FIG. 9 illustrates one such combination of dissimilar electrodes. As discussed previously, if an electrode is unused, then it must be covered and protected to prevent tissue damage or undesirable tissue growth into the stimulator. If threaded electrode hole 46 is unused, then it is filled with electrode plug 48, which is screwed tightly into hole 46, as illustrated in FIG. 10.

Figure 11:
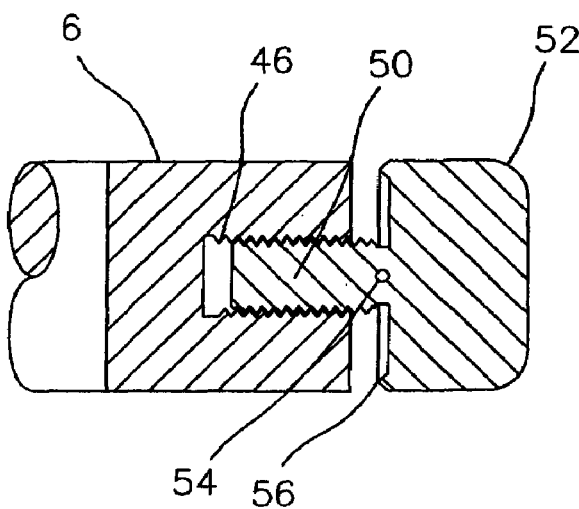
FIG. 11 is a longitudinal cross-section of a threaded hole electrode with plug.

A further method of attaching an electrically conductive wire 38 (not illustrated) to electrically conductive case end 6 is illustrated in FIG. 11, where threaded electrode hole 46 mates with smooth nut 52 by inserting threaded insert 50 into threaded electrode hole 46. As nut 52 is tightened, an electrically conductive wire, not illustrated, that has previously been inserted in smooth nut through-hole 54 is crushed between electrically conductive case end 6 and nut crush lip 56, thereby making contact between the electrically conductive wire and electrically conductive case end 6. Smooth nut through-hole 54 retains the wire in position and assures that the wire is secured in place until smooth nut 52 is fully tightened.

Figure 12:
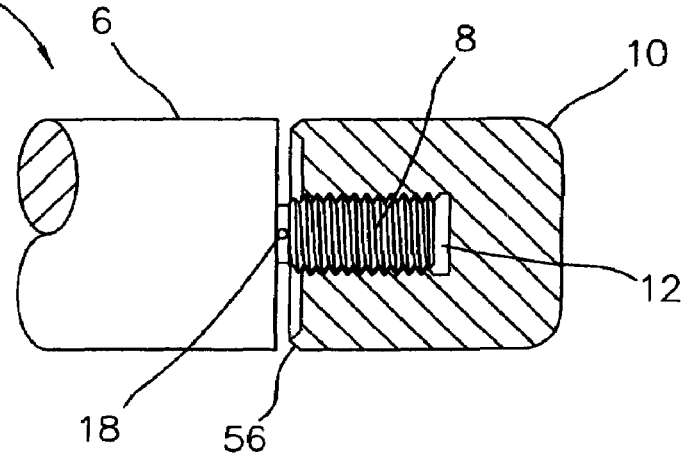
FIG. 12 is a longitudinal cross-section of a threaded pin electrode with nut.

Illustrated in FIG. 12 is an alternate embodiment of a method of attaching an electrically conductive wire to a miniature stimulator 2, wherein electrically conductive case end 6 has threaded electrically conductive electrode 8 attached thereto. Electrically conductive electrode 8 contains electrode through-hole 18 located proximate to electrically conductive case end 6. Protective nut 10 is attached to threaded electrically conductive electrode 8 by screwing electrically conductive electrode 8 into protective nut threaded hole 12. An electrically conductive wire, not shown, is held in place by placing it through electrode through-hole 18. The wire makes electrical contact with electrically conductive case end 6 by virtue of being crushed between electrically conductive case end 6 and protective nut 10 by nut crush lip 56.

Figure 13:
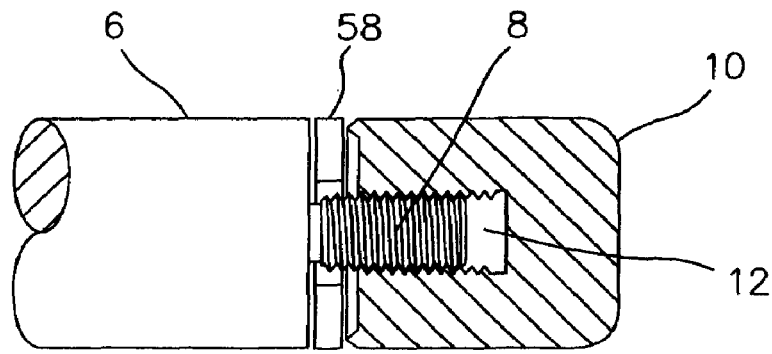
FIG. 13 is a longitudinal cross-section of a threaded pin electrode with nut and spade connector.

A further embodiment of methods to attach an electrically conductive wire (not illustrated) to assure electrical conductivity between the electrically conductive wire and the electrically conductive case end 6 is illustrated in FIG. 13, where spade clip 58, which is attached to an electrically conductive wire (not illustrated), is securely fastened between protective nut 10 and electrically conductive case end 6.

Figure 14:
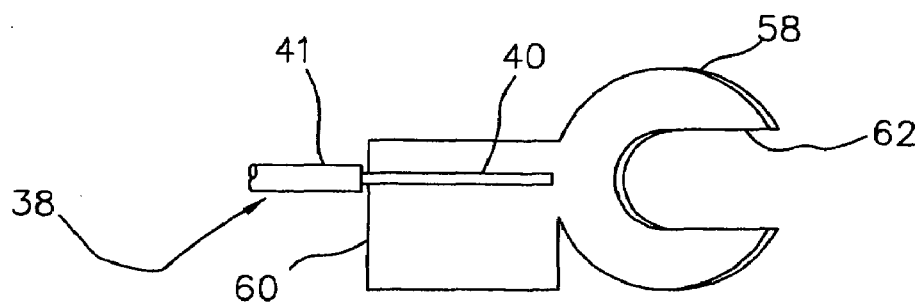
FIG. 14 illustrates a spade connector.

Spade clip 58 is shown in FIG. 14 with tab 60 configured to attach to electrically conductive wire 38. Electrically conductive wire 38, is placed in tab 60 with wire insulator 41 stripped from an end portion of the electrically conductive wire 38, thereby exposing wire conductor 40 for electrical contact with tab 60. Tab 60 is wrapped around electrically conductive wire 38 so as to assure that electrically conductive wire 38 is securely attached to spade clip 58 by wrapped tab 60, which has crimp 70, as shown in FIG. 15.

Figure 15:
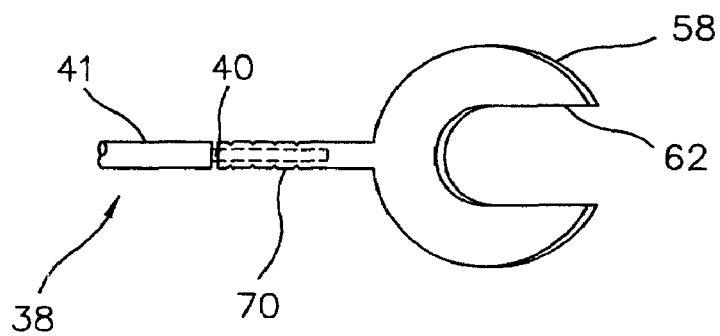
FIG. 15 illustrates a spade connector attached to a wire.
Figure 15A:
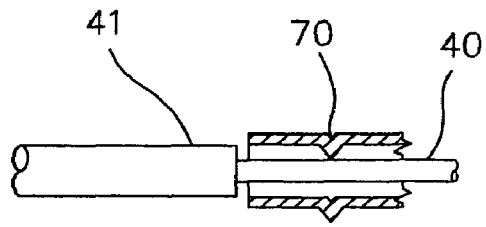
FIG. 15A illustrates a detailed section of the crimp of FIG. 15.
Figure 15B:
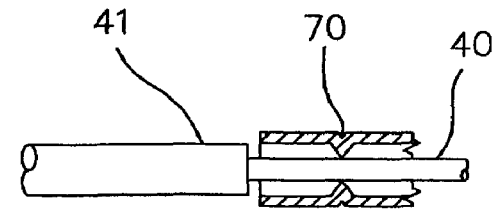
FIG. 15B illustrates a detailed section of an alternate crimp of FIG. 15.

FIG. 15 illustrates spade clip 58 with electrically conductive wire 38 attached to spade clip 58 and retained by crimp 70. Opening 62 in spade clip 58 is configured to approximate the diameter of electrically conductive electrode 8 (see FIG. 13) such that spade clip 58 fits over electrically conductive electrode 8 (not illustrated). In a preferred embodiment, tab 60 and electrically conductive wire 38 are oriented at a right angle to spade clip 58, thus assuring that electrically conductive wire 38 is parallel to the longitudinal axis of miniature stimulator 2, thereby minimizing stresses in the wire. FIGS. 15A and 15B illustrate detailed alternate crimp 70 attachment methods of securely fastening wire conductor 40 to spade clip 58.

Figure 16:
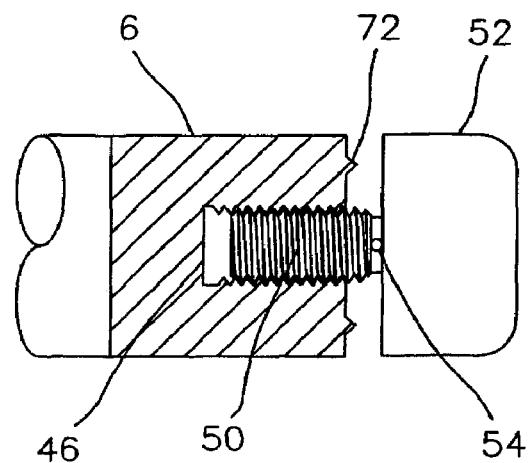
FIG. 16 is a longitudinal cross-section of an electrode hole with a plug and crush lip.

An alternate embodiment, illustrated by cross-sectional view in FIG. 16, has a wire (not shown) placed through smooth nut through-hole 54, which is located proximate to smooth nut 52. As smooth nut 52 is tightened into threaded electrode hole 46 by inserting threaded insert 50 into threaded electrode hole 46, the wire is crushed between end crush lip 72 and cap 52, thereby making electrical contact between the wire and electrically conductive case end 6. The difference between the method of wire attachment illustrated in FIG. 11 and that shown by FIG. 16 is the relocation of nut crush lip 56 from the protective nut 10 of FIG. 11 to electrically conductive case end 6, as end crush lip 72 in FIG. 16.

Figure 18:
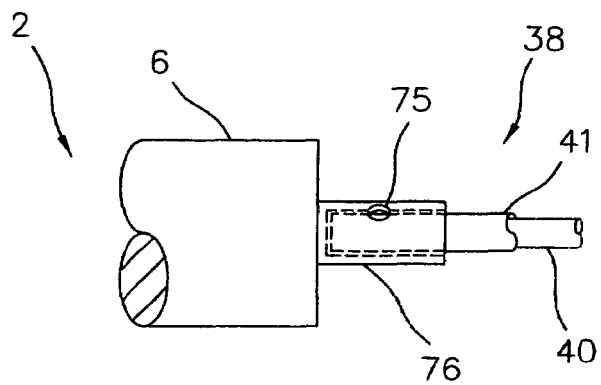
FIG. 18 illustrates a pin electrode with a wire inserted.
Figure 19:
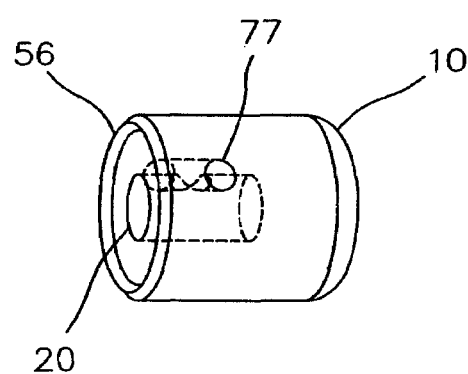
FIG. 19 illustrates a protective nut with a crush lip.

Illustrated in FIGS. 18 and 19 is a further embodiment of a method of attaching an electrically conductive wire (not shown) to miniature stimulator 2, wherein smooth electrode 76 contains no threads and also has offset electrode through-hole 75, which is aligned to lie in a plane that is perpendicular to the longitudinal axis of miniature stimulator 2 to intersect with the outer diameter of wire conductor 38, such that when a pin (not shown) is placed in through-hole 75, it will contact wire conductor 40, either by penetrating wire insulator 41 or by contacting the wire conductor 40 directly, if wire insulator 41 has been stripped from that area. Protective nut 10, shown in FIG. 19, illustrates nut crush lip 56, and also illustrates offset protective nut mounting hole 77, which aligns with offset electrode through-hole 75, thereby allowing a pin (not shown) to pass through both offset protective nut mounting hole 77 and offset electrode through-hole 75.

Figure 20:
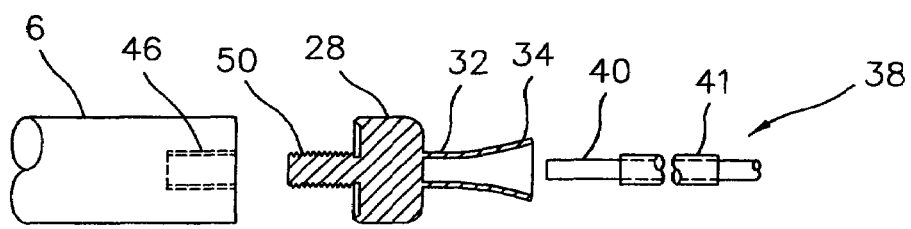
FIG. 20 is a longitudinal section through threaded insert with a flare attachment.

A further embodiment, illustrated by cross-sectional view in FIG. 20, is similar to the embodiment presented in FIG. 4, but with electrically conductive case end 6 having threaded electrode hole 46 in place of flare nut mounting hole 30. Threaded insert 50 is screwed into threaded electrode hole 46, thereby securing protective nut 28 to electrically conductive case end 6. An electrical connection between electrically conductive wire 38 is made by stripping wire insulator 41 from the end of wire 38 thus exposing wire conductor 40. Conductor 40 is inserted into flare nut wire receptor 32 using flare 34 as a guide. Wire insulator 41 is stripped such that, when wire conductor 40 is inserted fully into flare nut wire receptor 32, wire insulator 41 extends approximately one-quarter of the length of receptor 32 into receptor 32. Wire 38 is securely attached inside receptor 32 by crimping receptor 32 to wire conductor 40.

Figure 17:
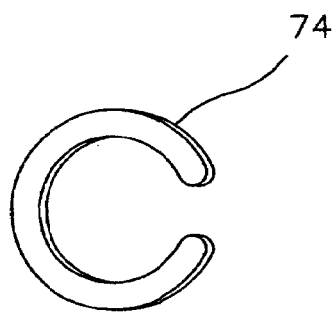
FIG. 17 illustrates a C-clamp.
Figure 21:
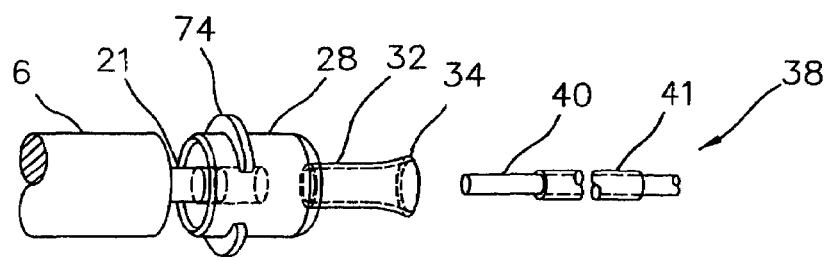
FIG. 21 is a perspective view of a stimulator in combination with a flare nut.

An alternate method of attaching protective nut 28 to smooth stud electrode 21 is illustrated in FIG. 21. While the preferred method of attaching the two components is by screwing them together, as illustrated in FIGS. 4 and 20, in the instant embodiment, electrically conductive case end 6 has stud electrode 21 attached thereto, which has no threads. Protective nut 28 slips snugly over stud electrode 21 until electrically conductive case end 6 is located touching adjoining protective nut 28. As previously illustrated in FIG. 20 and as discussed above, wire 38 and its conductor 40 and wire insulator 41 are securely fitted inside flare nut wire receptor 32 by using flare 34 as a guide. Electrically conductive wire 38 is secured by crimping flare nut wire receptor 32 onto wire conductor 40 (see FIG. 21). Protective nut 28 is secured to stud electrode 21 by placing C-clip 74 (see FIG. 17) over protective nut 28 such that protective nut 28 is partially deformed, thereby creating a secure attachment between stud electrode 21 and protective nut 28.

Figure 22:
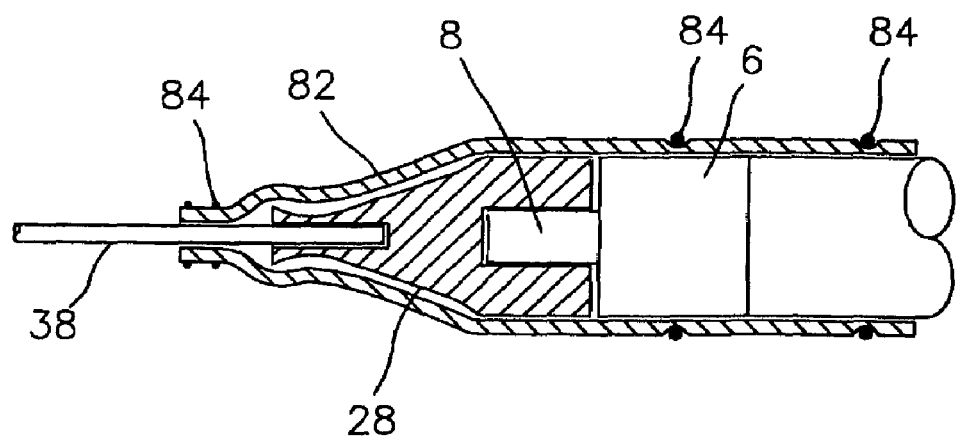
FIG. 22 is a longitudinal section showing the flare nut with a rubber boot.
Figure 22A:
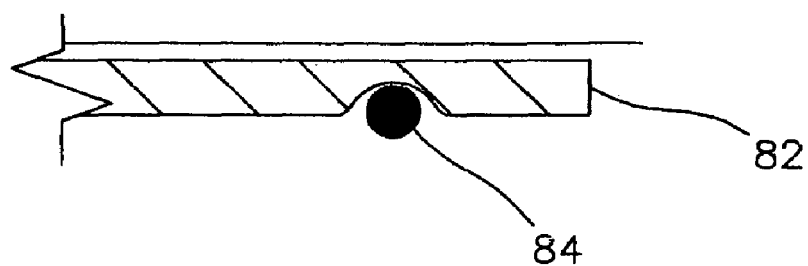
FIG. 22A is a section showing tie interaction with the rubber boot of FIG. 22.

The preferred method of assuring electrical insulation between electrically conductive case end 6, electrically conductive electrode 8, protective nut 28, and wire 38, as illustrated in FIG. 22, is to cover the electrically conductive case end 6 and other parts with rubber boot 82. Rubber boot 82 is made of a flexible insulating material that is biocompatible, such as silicone. Its purpose is to provide electrical insulation such that stray electrical signals do not pass between surrounding tissue and any electrically conductive part of the device. Rubber boot 82 is secured to the device, preferably by tying it in place with ties 84. A sufficient number of ties 84 are placed by the surgeon to assure that that the rubber boot 82 will not move. It is preferred that at least one tie 84 and, preferably two or more ties 84, be placed on rubber boot 82 to secure rubber boot 82 to insulating case 4, so as to electrically insulate electrically conductive case end 6 from the living tissue. FIG. 22A illustrates a typical tie 84 interacting with rubber boot 82, so as to establish and maintain a hermetic seal. Alternate methods of attaching rubber boot 82 include the use of ridges inside rubber boot 82, clamps over rubber boot 82, silicone adhesive inside rubber boot 82, ridges on the outside of insulating case 4, a male notch with matching female indentation forming an O-ring seal, and the tight fit of rubber boot 82 over the device, either with or without internal ridges.

Figures 23, 24:
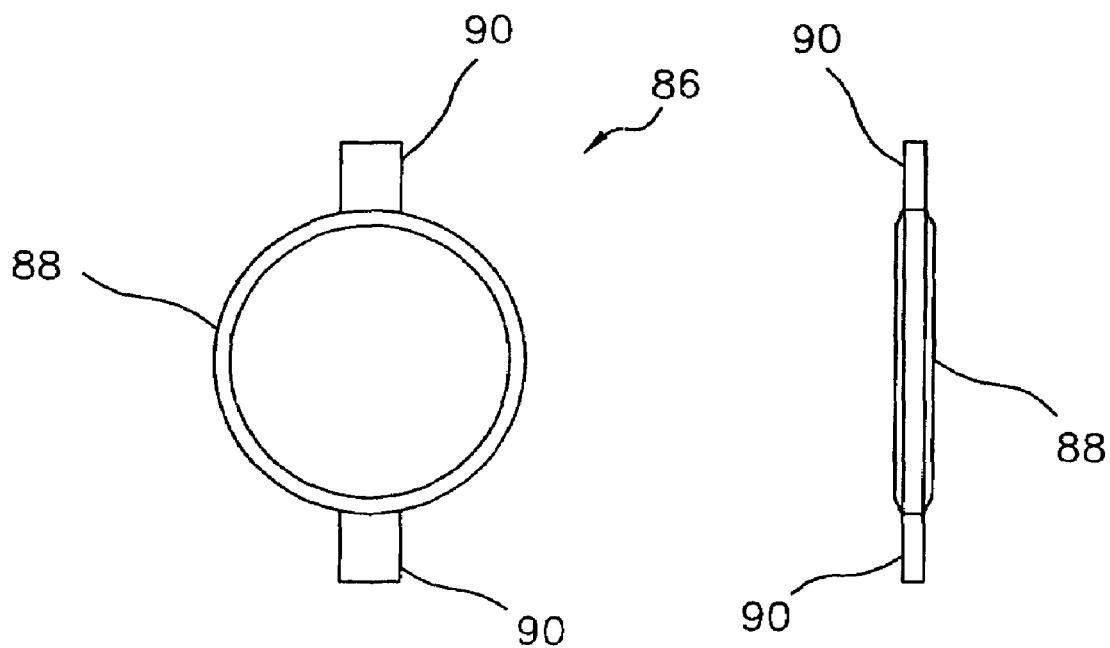
FIG. 23 is a top view of a disk-shaped miniature stimulator with electrodes.
FIG. 24 is a side view of a disk-shaped miniature stimulator with electrodes.

An alternate configuration to miniature stimulator 2, previously illustrated in FIG. 1, is miniature disk stimulator 86, which is illustrated in FIGS. 23 and 24. Disk 88 is preferably comprised of insulating material having at least one electrically conductive electrode 90. Two electrodes are illustrated in FIGS. 23 and 24, but alternate arrangements have at least one, e.g., 1 to 8 or more, electrodes. Electrode 90 is hermetically bonded to disk 88. Electrode 90 can be one or more tabs as shown in FIG. 23, or it can be one or more flush electrodes (not illustrated) that are mounted on the surface of disk 88. While the tabs 90 that are illustrated in FIGS. 23 and 24 project from the surface of the insulating disk 88, the tabs 90 can equally well not project from the surface of insulating disk 88 and may be contiguous with the surface such that they do not project above the surface. The methods of connecting a wire to the miniature stimulator that have been previously discussed are equally applicable to miniature disk stimulator 86, as well as to other configurations. The dimensions of disk 88 are about 5 to 40 mm diameter and about 1 to 6 mm thick. Electrically conductive electrode 90 is preferably made of an electrical conductor that is biocompatible and corrosion resistant, such as platinum, iridium, platinum-iridium, tantalum, titanium or a titanium alloy, stainless steel, niobium, or zirconium. Disk 88 is made of an electrical insulator that is biocompatible, such as ceramic, glass, or plastic.

Figure 25:
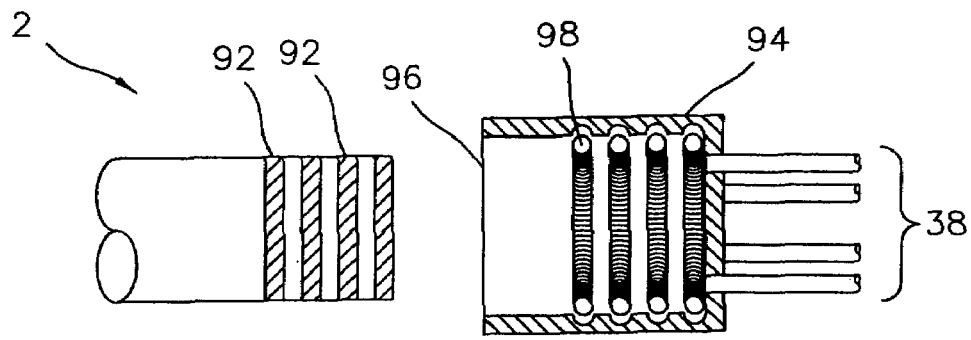
FIG. 25 illustrates a miniature stimulator annular electrode and a section through the annular nut.

FIG. 25 illustrates an alternate annular electrode arrangement on the end of miniature stimulator 2. At least one annular electrode may be used, e.g., four annular electrodes 92 are illustrated in FIG. 25. Each annular electrode 92 is capable of carrying an independent electrical signal and is electrically isolated from the other electrodes. The signal from or to stimulator 2 passes along electrically conductive wires 38, where each electrically conductive wire 38 carries an independent signal and is electrically isolated from the others. Each electrically conductive wire 38 corresponds with and is connected to one annular electrode 92 by means of its connecting to toroidal spring 98. Alternatively, toroidal spring 98 may be a semi-circular spring. Annular cap 94 contains toroidal springs 98. Electrically conductive wires 38 pass through holes in the end of cap 94. The internal diameter of annular cap opening 96 approximates but is slightly larger than the outer diameter of stimulator 2. To make a connection between annular electrode 92 and toroidal spring 98, annular cap 94 is pushed in a longitudinal direction along the axis of stimulator 2 until it is fully engaged in a position such that electrical contact is made between annular electrode 92 and a corresponding toroidal spring 98. Each toroidal spring 98 is preferably retained inside annular cap 94 by an annular recession inside annular cap 94 such that during engagement of stimulator 2 with annular cap 94, the toroidal spring 98 is forced into the recession, thereby allowing room for smooth engagement of the parts. The alignment of toroidal spring 98 and annular electrode 92 is such that each toroidal spring 98 contacts only one corresponding annular electrode 92.

Figures 26, 27:
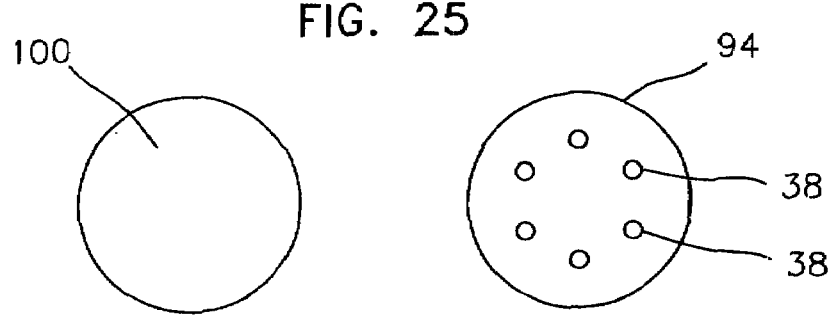
FIG. 26 is an end view of the miniature stimulator with annular electrodes.
FIG. 27 is an end view of the annular nut.
Figure 28:
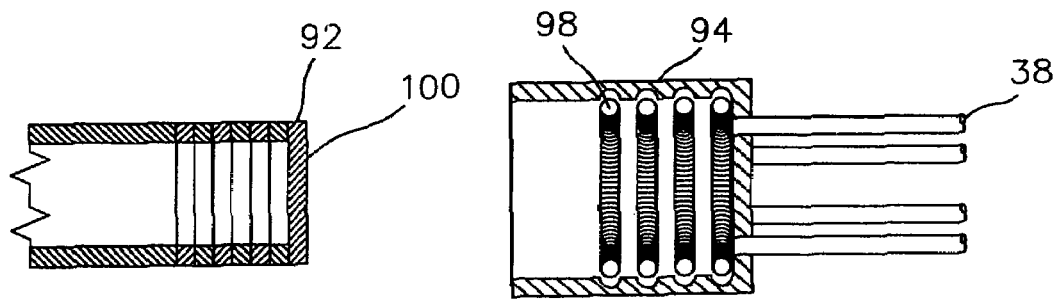
FIG. 28 is a longitudinal section through a miniature stimulator with annular electrodes and a section through the annular nut.

FIG. 26 illustrates the case end 100 of stimulator 2 and FIG. 27 illustrates the end view of annular cap 94. A cross-sectional view of annular electrode 92 is illustrated in FIG. 28.

Figures 29, 30:
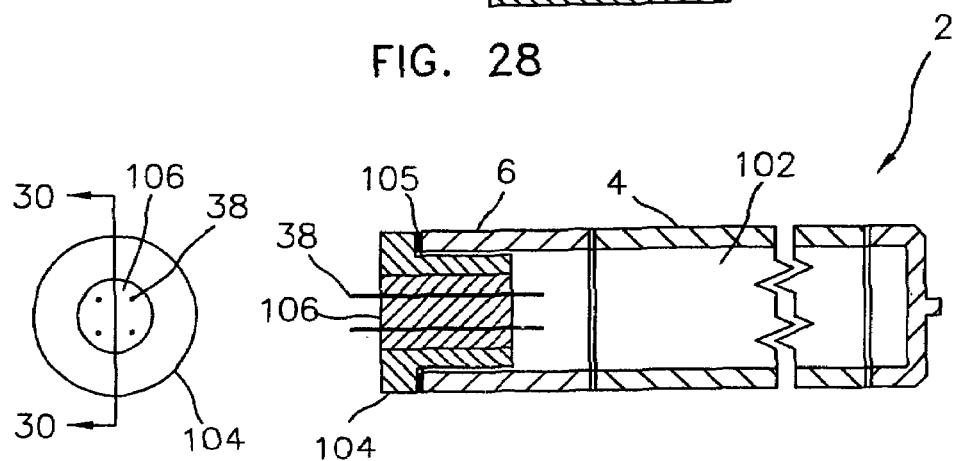
FIG. 29 illustrates an end view of a plug with wires.
FIG. 30 is a longitudinal cross-section through a plug with wires installed in a hollow miniature stimulator.

Another embodiment for making an electrical connection to miniature stimulator 2 is illustrated in FIGS. 29 and 30. FIG. 29 illustrates an end view of electrode plug 104 (see FIG. 30) showing four electrically conductive wires 38 passing into the center of electrode plug 104 through potting material 106. The potting material provides a secure, hermetic seal for wires 38 to pass into miniature stimulator core 102, as illustrated in FIG. 30.

FIG. 30 illustrates a longitudinal view in cross-section of miniature stimulator 2 comprising insulating case 4, electrically conductive case end 6, electrode plug 104, and potting material 106. Electrode plug 104 is made of a biocompatible material such as titanium and is attached by weld 105 to electrically conductive case end 6, thereby forming a hermetic seal.

Figure 31:
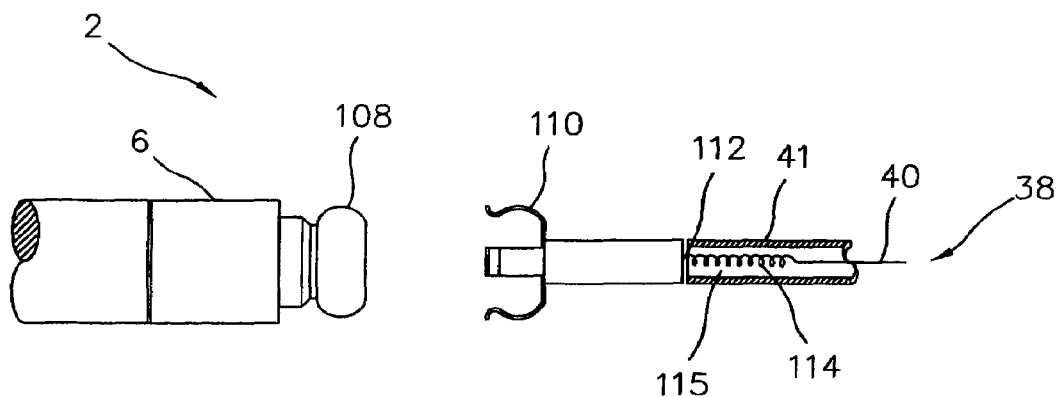
FIG. 31 illustrates a perspective view of an electrically conductive doorknob shaped electrode with spring clip connector and wire.

Another embodiment for making an electrical connection to a miniature stimulator 2 is illustrated in FIG. 31 where doorknob electrode 108 is intimately attached to electrically conductive case end 6. The doorknob electrode is made of a material that is electrically conductive and biocompatible, such as titanium. Spring clip 110 is preferably a clip made of titanium which has two or more, and preferably three or four prongs. Wire insulator 41 is stripped from the end of wire 38 thereby exposing wire conductor 40. Wire conductor 40 is preferably attached to spring clip 110 by strain relief weld 112. Strain relief weld 112 helps to relieve strain in wire conductor 40 by virtue of being oriented perpendicular to the longitudinal axis of miniature stimulator 2. Further strain relief is provided in wire conductor 40 by virtue of it being tightly coiled inside wire insulator 41 thereby forming wire strain relief 114. The inside of wire insulator 41 is fill material 115, which is preferably soft silicone, to minimize infiltration of body fluids and other tissue inside wire 38.

Figure 32:
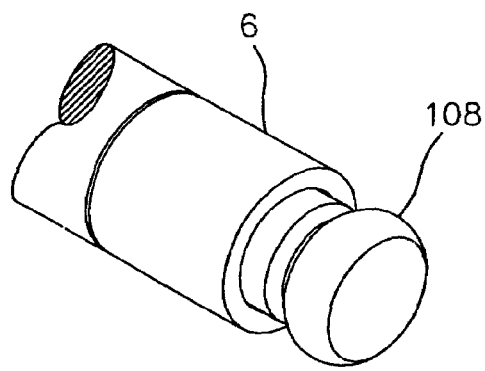
FIG. 32 is a perspective view of the electrically conductive doorknob shaped electrode.
Figure 33:
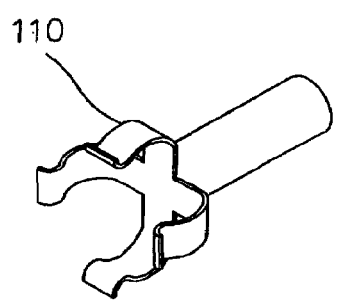
FIG. 33 is a perspective view of the spring clip connector.

A perspective view of doorknob electrode 108, showing its end attached to electrically conductive case end 6, is illustrated in FIG. 32. FIG. 33 illustrates a perspective view of spring clip 110 showing the four prongs that slip over doorknob electrode 108 to form an electrical connection.

Figure 34:
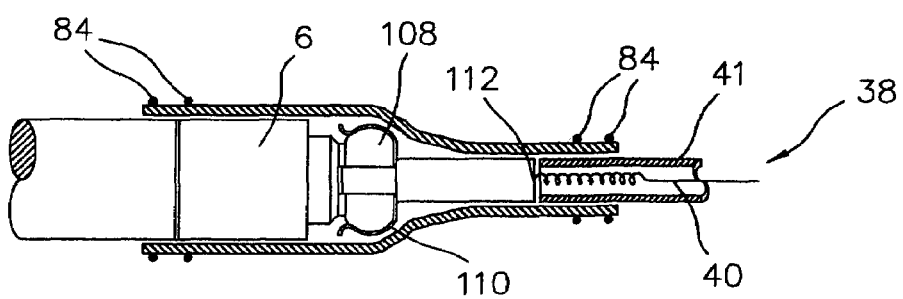
FIG. 34 is a longitudinal section through the doorknob shaped connector with a wire and rubber boot.

FIG. 34 illustrates spring clip 110 together with electrically conductive wire 38, which in turn is attached by strain relief weld 112 to wire conductor 40. Spring clip 110 is shown in its attached position on doorknob electrode 108. Rubber boot 82 is securely fastened to the device with ties 84 to completely cover electrically conductive case end 6, doorknob electrode 108, wire conductor 40 and a portion of wire insulator 41, thus electrically insulating the body tissue from electrical signals.

Figure 35:
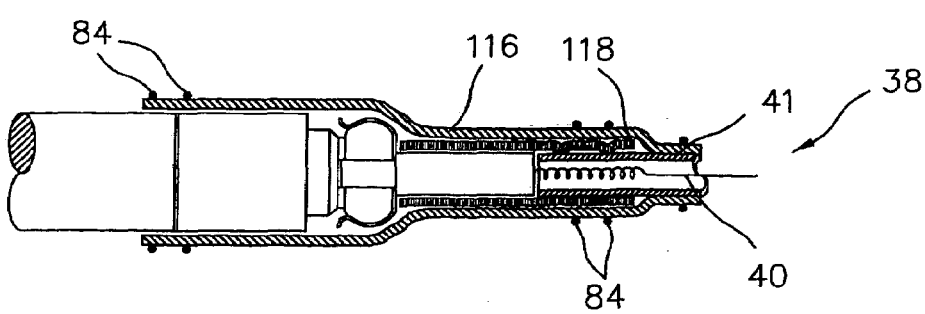
FIG. 35 is a longitudinal section through the doorknob shaped connector with crimped connector a wire and rubber boot.

An alternate embodiment is presented in FIG. 35, which is similar to the connection device presented in FIG. 34 except that connector crimp 118, which is selected from the group of biocompatible materials, and is preferably platinum metal, is placed over the end of electrically conductive wire 38 so as to cover a portion of wire insulator 41 and stripped wire conductor 40. Connector crimp 118 is attached to electrically conductive wire 38 by crimping it onto wire 38.

Figure 36:
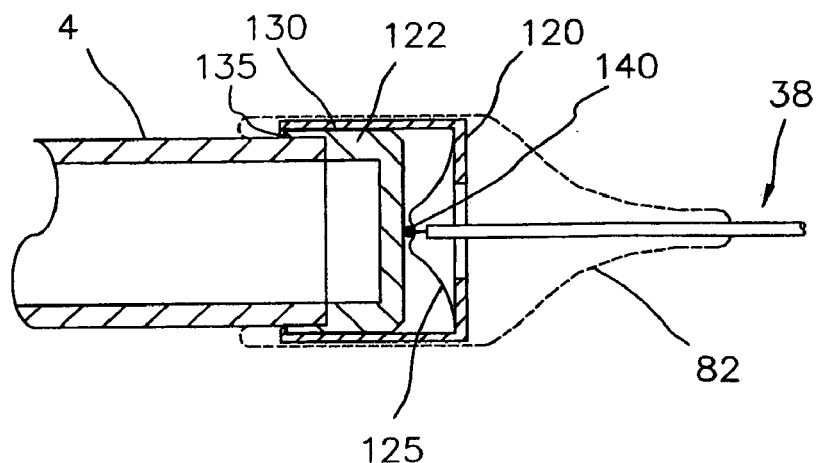
FIG. 36 is longitudinal section through the snap-on cap connector with rubber boot.

A preferred embodiment is shown in FIG. 36 in which slip-on cap 122 has a slightly larger internal diameter of a portion of slip-on cap 122 such that it slips over the outer diameter of insulating case 4. Snap-on cap 120 has at least one flexible member 130 having a tooth 135 on each flexible member 130. Tooth 135 engages the edge of electrically conductive slip-on cap 122, as illustrated in FIG. 37A, and holds snap-on cap 120 tightly in place. Electrical conductivity is achieved between electrically conductive wire 38 and electrically conductive slip-on cap 122 by spring disk 125 holding enlarged end of wire 140 tightly in contact with electrically conductive slip-on cap 122 when snap-on cap 120 is in place. Rubber boot 82 provides electrical insulation by covering electrically conductive slip-on cap 122, snap-on cap 120, and a portion of electrically conductive wire 38.

Figure 37:
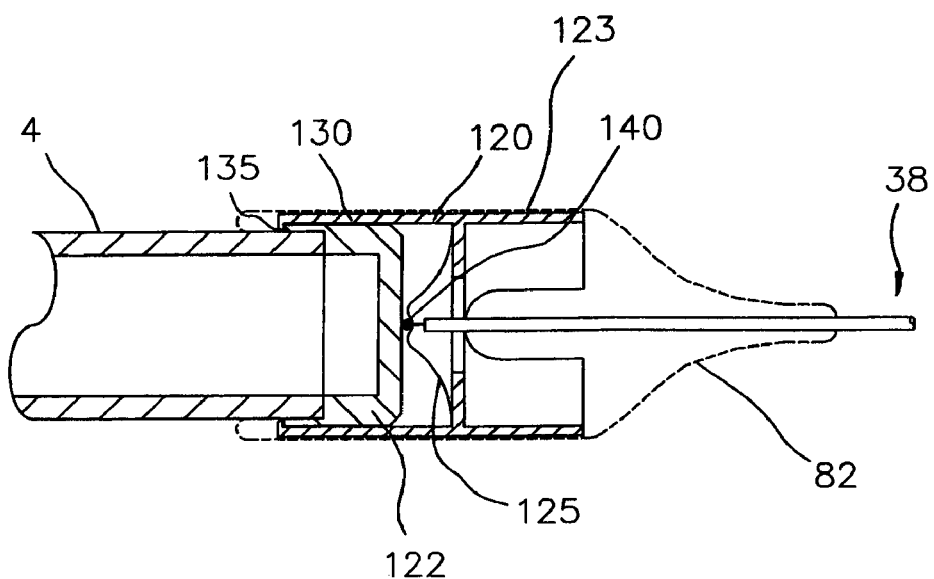
FIG. 37 is longitudinal section through the elongated snap-on cap connector with rubber boot.
Figure 37A:
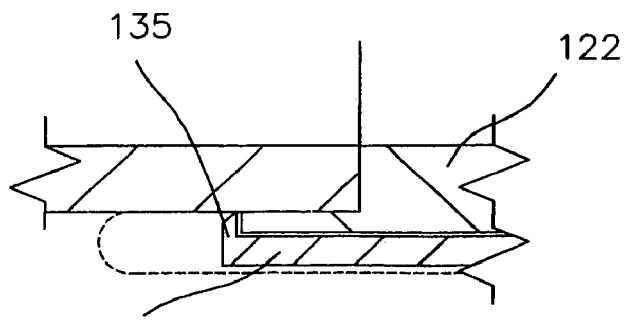
FIG. 37A details the tooth interaction with the slip-on cap of FIG. 37.

An alternate embodiment is shown in FIG. 37 in which snap-on cap 120 is elongated and slotted on the end opposite tooth 135. When slotted elongated end 123 is squeezed, flexible members 130 are levered outward and tooth 135 is thereby disengaged from the edge of slip-on cap 122. FIG. 37A illustrates the interaction of tooth 135 with slip-on cap 122 such that snap-on cap 120 is securely fastened to slip-on cap 122.

Figure 38:
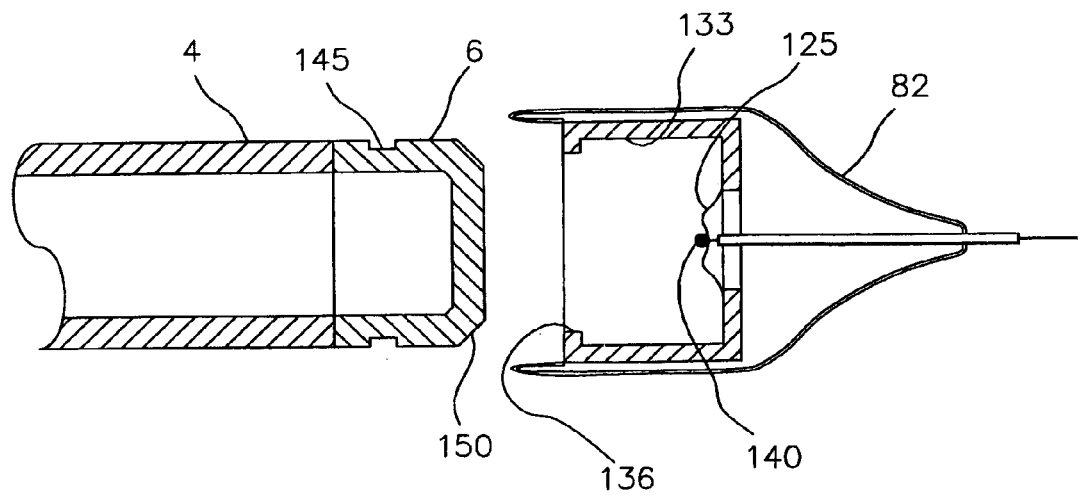
FIG. 38 is longitudinal section through the flat-bottomed slot connector with rubber boot.
Figures 39, 40:
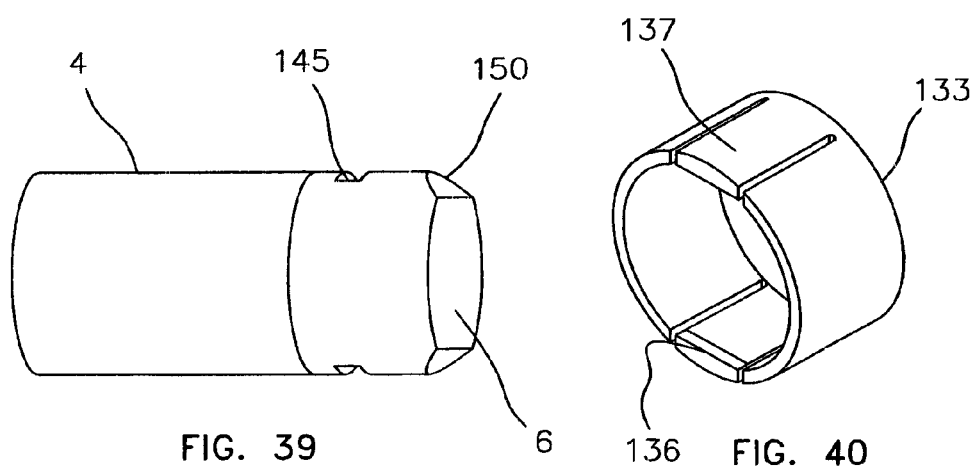
FIG. 39 is a perspective view of the flat-bottomed slot connector.
FIG. 40 is a perspective view of the flat-bottomed snap-on cap.

An alternate embodiment is shown in FIG. 38 in which electrically conductive case end 6 contains at least one angled flat 150 to allow rotatable cap tooth 136 of rotatable cap 133 to slide smoothly onto the end of electrically conductive case end 6 and to facilitate alignment of rotatable cap tooth 136 with flat-bottomed slot 145. Electrically conductive case end 6 has at least one flat-bottomed slot 145 that engages rotatable cap tooth 136 of rotatable cap 133 to retain rotatable cap 133 on electrically conductive case end 6. When rotatable cap 133 is rotated about its longitudinal axis by about 30° to 90°, rotatable cap tooth 136 is rotatably moved out of flat-bottomed slot 145, thereby allowing rotatable cap 133 to be removed. These elements are shown in the perspective views of FIGS. 39 and 40, the angled flat 150 is indicated to facilitate placement of rotatable cap 133 onto electrically conductive case end 6 in order to engage rotatable cap tooth 136 with flat-bottomed slot 145.

Figures 41, 42:
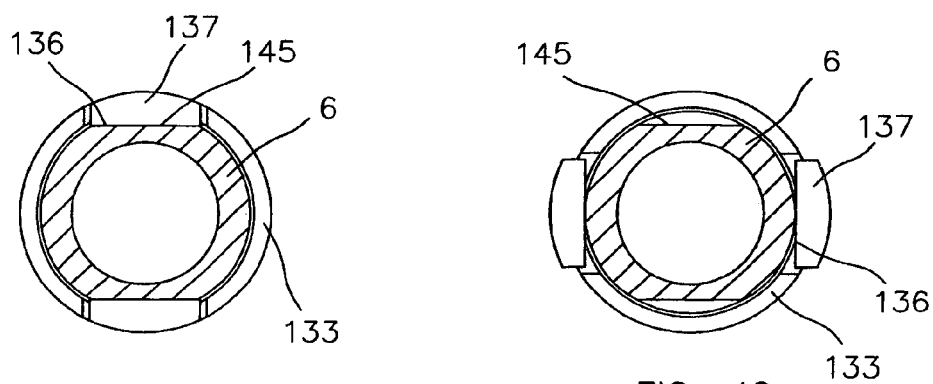
FIG. 41 is a cross-section of the flat-bottomed slot connector in the engaged position.
FIG. 42 is a cross-section of the flat-bottomed slot snap-on cap in the disengaged position.

A cross-sectional view, through flat-bottomed slot 145 and perpendicular to the longitudinal axis, is presented in FIGS. 41 and 42. The view of FIG. 41 indicates the position when rotatable cap 133 is in position to engage rotatable cap tooth 136 with flat-bottomed slot 145. The view of FIG. 42 indicates the same cross-sectional view as in FIG. 41 but rotatable cap 133 has been rotated 90° from the position illustrated in FIG. 41 to disengage rotatable cap tooth 136 from flat-bottomed slot 145 thereby allowing removal of rotatable cap 133.

These various embodiments are of devices and methods for connecting an electrically conductive wire to a miniature, implantable stimulator in order to efficiently transmit or receive an electrical signal that is associated with the implantable stimulator.

Obviously, these methods of attaching a wire to a miniature implantable stimulator can be used in permutations and combinations not specifically discussed herein. Many modifications and variations of the present invention are possible in light of the above teachings. It is therefore to be understood that, within the scope of the appended claims, the invention may be practiced otherwise than as specifically described.

What is claimed is:

1. A method of communicating electrical signals between living tissue and an implantable miniature device configured for monitoring and/or affecting body parameters, comprising:
   snapping a spring clip means over a doorknob electrode; and
   attaching a conductive wire having a first end configured for electrical coupling to a selected portion of living tissue and a second end configured for coupling to said spring clip means.

2. The method of claim 1, further comprising selecting said spring clip means to include welding said conductive wire second end.

3. The method of claim 1, further comprising selecting said spring clip means to include at least one prong for grasping said doorknob electrode.

4. The method of claim 1, further comprising placing an insulating rubber boot over said spring clip means and said doorknob electrode.

5. The method of claim 1, further providing said doorknob electrode formed of a material selected from the group consisting of titanium, titanium alloy, platinum, iridium, platinum-iridium, stainless steel, tantalum, and niobium.

6. A method of communicating electrical signals between living tissue and an implantable miniature device configured for monitoring and/or affecting body parameters, comprising:
   snapping a spring clip connector over a doorknob electrode; and
   attaching a conductive wire having a first end configured for electrical coupling to a selected portion of living tissue and a second end configured for coupling to said spring clip connector.

7. The method of claim 6, further implanting said first end of said conductive wire where it is in contact with living tissue.

8. The method of claim 6, further implanting said miniature implantable device in living tissue remote from said first end of said conductive wire.

9. The method of claim 6, further comprising placing an insulating rubber boot over said spring clip connector.

10. The method of claim 9, further providing said rubber boot comprised of silicone.

11. The method of claim 6, further providing said spring clip connector formed of a material selected from the group consisting of titanium, titanium alloy, platinum, iridium, platinum-iridium, stainless steel, tantalum and niobium.

12. The method of claim 6, further providing said doorknob electrode formed of a material selected from the group consisting of titanium, titanium alloy, platinum, iridium, platinum-iridium, stainless steel, tantalum, and niobium.

13. The method of claim 6, further providing said spring clip connector having at least one prong for grasping said doorknob electrode.

14. The method of claim 6, providing said spring clip connector that is adapted for attaching said conductive wire thereto for communicating electrical signals between said doorknob electrode and tissue.

15. The method of claim 6, further comprising placing an insulating rubber boot over said spring clip connector, said conductive wire second end, and the doorknob electrode.

* * * * *